United States Patent
Mitsuhashi et al.

(10) Patent No.: US 12,318,069 B2
(45) Date of Patent: Jun. 3, 2025

(54) INSERTION APPARATUS AND ENDOSCOPE

(71) Applicant: OLYMPUS CORPORATION, Tokyo (JP)

(72) Inventors: Keita Mitsuhashi, Hachioji (JP); Tsukasa Ota, Hachioji (JP); Takuto Yoshinaga, Hino (JP); Wataru Matsuura, Fuchu (JP); Motohiko Suzuki, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 366 days.

(21) Appl. No.: 17/835,237

(22) Filed: Jun. 8, 2022

(65) Prior Publication Data

US 2022/0296077 A1    Sep. 22, 2022

Related U.S. Application Data

(63) Continuation of application No. PCT/JP2019/048814, filed on Dec. 12, 2019.

(51) Int. Cl.
*A61B 1/005* (2006.01)
*A61B 1/00* (2006.01)

(52) U.S. Cl.
CPC .......... *A61B 1/005* (2013.01); *A61B 1/00114* (2013.01)

(58) Field of Classification Search
CPC ............................ A61B 1/005; A61B 1/00114
USPC ....................................................... 600/526
See application file for complete search history.

(56) References Cited

U.S. PATENT DOCUMENTS

| | | | |
|---|---|---|---|
| 6,951,537 B2 * | 10/2005 | Hirata | A61B 1/0055 600/152 |
| 7,922,650 B2 | 4/2011 | McWeeney et al. | |
| 2004/0122360 A1 | 6/2004 | Waldhauser et al. | |
| 2018/0228346 A1 | 8/2018 | Sekowski et al. | |
| 2019/0254504 A1 | 8/2019 | Ide | |

FOREIGN PATENT DOCUMENTS

| | | |
|---|---|---|
| JP | H07-108037 A | 4/1995 |
| JP | 2001-112707 A | 4/2001 |
| JP | 2009-219795 A | 10/2009 |
| JP | 2010-035621 A | 2/2010 |
| JP | 2014-014610 A | 1/2014 |
| WO | 2004/058341 A2 | 7/2004 |
| WO | 2018/131204 A1 | 7/2018 |

OTHER PUBLICATIONS

International Search Report dated Feb. 25, 2020 received in PCT/JP2019/048814.

* cited by examiner

*Primary Examiner* — Nadia A Mahmood
(74) *Attorney, Agent, or Firm* — Scully, Scott, Murphy & Presser, P.C.

(57) ABSTRACT

An insertion apparatus in the invention includes: a multi-lumen tube provided in an insertion portion and formed in a bendable manner, the insertion portion being inserted into a subject; a distal end member arranged so as to cover a distal end of the multi-lumen tube; a braided tube into which the multi-lumen tube is inserted, a distal end edge portion of the braided tube being disposed between the distal end member and the multi-lumen tube; and a wire configured to bend the multi-lumen tube by traction, in which the braided tube includes a gap through which the wire passes from an outside of the braided tube to an inside of the braided tube.

20 Claims, 7 Drawing Sheets

INSERTION APPARATUS AND ENDOSCOPE

CROSS REFERENCE TO RELATED APPLICATION

This application is a continuation application of PCT/JP2019/048814 filed Dec. 12, 2019, the entire contents of which are incorporated herein by this reference.

BACKGROUND OF THE INVENTION

1. Field of the Invention

The invention relates to an insertion apparatus and an endoscope, in which an insertion portion configured to be inserted into a subject is configured using a multi-lumen tube formed in a bendable manner.

2. Description of the Related Art

In recent years, an endoscope that is a kind of insertion apparatus has been widely used, for example, in a medical field. The endoscope is an insertion apparatus configured such that a surface of an organ in a body cavity as a subject can be observed by inserting an elongated insertion portion into the body cavity. Moreover, the endoscope is an insertion apparatus configured such that various treatments can be performed to a desired site in the body cavity as an examination object or details of a desired site in the body cavity can be observed in more detail by inserting various treatment instruments or a miniature endoscope into the body cavity through a treatment instrument channel or the like provided on the endoscope as necessary.

In an endoscope that is this kind of insertion apparatus, in recent years, for example, various endoscopes configured using a multi-lumen tube have been proposed and put to practical use. By the multi-lumen tube, the insertion portion is formed in a bendable manner.

As insertion portions of conventional endoscopes, various insertion portions each of which is configured as a three-layer structure constituted by an insertion tube including a bending portion formed in a bendable manner, a braided tube externally provided so as to cover an outer surface of the insertion tube, and an outer sleeve sheathing an outer surface of the braided tube have been proposed and disclosed in U.S. Pat. No. 7,922,650 and Japanese Patent Application Laid-Open Publication No. 2001-112707 and the like. In the insertion portion having such a three-layer structure, the braided tube is provided for enhancing the strength and torsional rigidity of the insertion tube.

The insertion portion of the insertion apparatus disclosed in U.S. Pat. No. 7,922,650 is configured as a three-layer structure in which an outer surface of the multi-lumen tube formed in a bendable manner is sheathed with the braided tube and the outer surface of the braided tube is sheathed with the outer sleeve. A distal end edge portion of the braided tube is configured to be fixed at a distal end portion of the insertion portion while being sandwiched between the outer sleeve and the multi-lumen tube.

The bending portion of the insertion portion of the insertion apparatus disclosed in Japanese Patent Application Laid-Open Publication No. 2001-112707 is configured as a three-layer structure in which an outer surface of a bending tube constituted by a plurality of node rings is sheathed with the braided tube and the outer surface of the braided tube is sheathed with the outer sleeve. At the distal end portion of the insertion portion, the distal end edge portion of the braided tube is disposed on a distal end side of the bending portion, and a thread-winding binding fixation of the distal end edge portion is performed on an outer circumference surface of a metallic ring-shaped member to which a distal end of a bending wire is fixed. The outer surface of the braided tube is configured so as to be sheathed with the outer sleeve.

SUMMARY OF THE INVENTION

An insertion apparatus in an aspect of the present invention includes: a multi-lumen tube provided in an insertion portion and formed in a bendable manner, the insertion portion being inserted into a subject; a distal end member arranged so as to cover a distal end of the multi-lumen tube; a braided tube into which the multi-lumen tube is inserted, a distal end edge portion of the braided tube being disposed between the distal end member and the multi-lumen tube; and a wire configured to bend the multi-lumen tube by traction, in which the braided tube includes a gap through which the wire passes from an outside of the braided tube to an inside of the braided tube.

An endoscope in an aspect of the present invention includes: a multi-lumen tube provided in an insertion portion and formed in a bendable manner, the insertion portion being inserted into a subject; a distal end member arranged so as to cover a distal end of the multi-lumen tube; a braided tube into which the multi-lumen tube is inserted, a distal end edge portion of the braided tube being disposed between the distal end member and the multi-lumen tube; and a wire configured to bend the multi-lumen tube by traction. The braided tube includes a gap through which the wire passes from an outside of the braided tube to an inside of the braided tube.

DETAILED DESCRIPTION OF THE PREFERRED EMBODIMENTS

Figure 1:
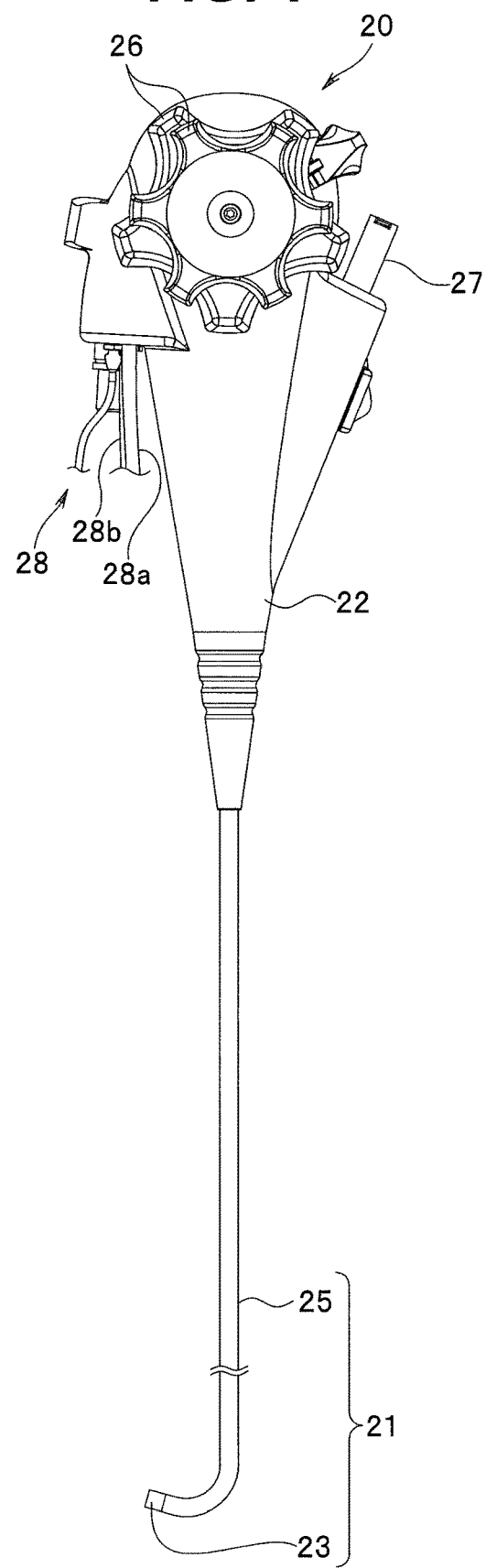
FIG. 1 is a plan view showing a schematic configuration of an endoscope that is an insertion apparatus in a first embodiment of the present invention.

Generally, a configuration in which an outer surface side of an insertion tube is sheathed with a braided tube is well known. The braided tube that is used in a conventional insertion apparatus is formed by weaving an element wire member formed of metal, a carbon-based fiber or the like in a grid pattern. Therefore, a distal end edge portion of the braided tube is in a state where a woven portion easily frays, where the shape is not stable and where a sharp end portion of the element wire member is exposed.

Therefore, in the case of employing the conventional well-known configuration disclosed in U.S. Pat. No. 7,922, 650 and Japanese Patent Application Laid-Open Publication No. 2001-112707 and the like, there is fear that an element wire member end portion of the distal end edge portion of the braided tube cuts through the outer sleeve and protrudes toward the outer surface of the outer sleeve. This causes a problem that the watertight property of the distal end portion of the insertion portion cannot be maintained.

Further, in the case where the insertion portion of the endoscope is used in a state where the element wire member end portion of the distal end edge portion of the braided tube protrudes to the outer surface of the outer sleeve, there is fear that a mucous membrane in the body cavity is damaged or bleeding occurs, for example. Hence, for example, by increasing the thickness of the outer sleeve, it is possible to prevent the protrusion of the element wire member end portion of the distal end edge portion of the braided tube. However, in the case of such a configuration, a problem of increase in the diameter of the distal end portion of the insertion portion arises.

Meanwhile, as a contrivance for preventing fraying of the distal end edge portion of the braided tube, for example, it is possible to fix the distal end edge portion of the braided tube to the outer circumference surface of the metallic ring-shaped member provided at the distal end portion by thread-winding binding fixation, brazing fixation treatment or the like.

However, in the case where the fixation treatments are performed, there is a problem that an outer diameter of a thread-winding binding part or a brazing part becomes large. At the same time, there is a problem that production treatment equipment is separately needed, and in addition, there is a problem that a high-level treatment skill is required and therefore production cost rises.

Hence, as the insertion apparatus and the endoscope, each including the insertion portion using the multi-lumen tube, the present invention can provide an insertion apparatus and an endoscope, each of which makes it possible to surely prevent the distal end edge portion of the braided tube from protruding from the outer sleeve to the exterior, to restrain the increase in the diameter of the insertion portion, to secure of the watertight property of the distal end portion, and to obtain a safe and suitable insertion property.

The present invention will be described below with illustrated embodiments.

Each drawing to be used in the following description is schematically shown, and for showing each component element in a size that allows each component element to be recognized on the drawing, the dimensional relation, scale and others of each member are sometimes shown so as to be different fix each component element. Accordingly, in the present invention, the quantity of each component element described in each drawing, the shape of each component element, the size proportion of each component element, and the relative position relation of each component element are not limited to illustrated forms.

First Embodiment

FIG. 1 is a plan view showing a schematic configuration of an endoscope that is an insertion apparatus in a first embodiment of the present invention.

First, the endoscope that is the insertion apparatus in the present embodiment is an insertion apparatus for observing details of a desired site in a body cavity as an examination object by inserting an insertion portion into the body cavity through a treatment instrument channel (not illustrated) provided on a mother endoscope (not illustrated) having a conventionally general configuration, and is an example of a so-called baby endoscope. In this case, for example, the baby endoscope is a type of disposable insertion apparatus that is discarded after use.

Note that illustration of the mother endoscope and detailed descriptions of a configuration of the mother endoscope are omitted and only brief descriptions will be shown below assuming that an endoscope having a conventionally general configuration is applied to the mother endoscope.

The mother endoscope (not illustrated) to which an endoscope 20 (see FIG. 1) in the present embodiment is applied is an endoscope having a general form and configured to include an insertion portion having an elongated shape and configured to be inserted into a subject and an operation portion joined to a proximal end of the insertion portion.

The insertion portion is formed such that a distal end portion, a, bending portion and a flexible tube portion are continuously provided in order from a distal end side. In an interior of the distal end portion, for example, an image pickup unit constituted by an objective optical system and an image sensor such as a CCD or a CMOS, and an illumination optical system configured to forward emit illumination light transmitted using a light guide bundle are arranged.

At the distal end portion, a plurality of opening portions are provided. One of the opening portions communicates with a distal end of a treatment instrument channel configured to allow insertion of the insertion portion.

The bending portion is assembled such that a plurality of bending pieces are continuously provided, and is configured to be capable of being actively bent in all directions around an insertion axis. The flexible tube portion is configured by a tubular member formed in a passively bendable manner.

A treatment instrument insertion portion is provided on the operation portion, and the treatment instrument insertion portion communicates with a proximal end of the treatment instrument channel of the insertion portion. Further, a plurality of operation members such as a bending operation knob for performing a bending operation of the bending portion, and the like are provided in the operation portion.

A universal cable extends from the operation portion. A connector configured to allow attachment and detachment with an external apparatus (not illustrated) such as a light source device is provided at a distal end of the universal cable.

The endoscope 20 in the present embodiment is a baby endoscope that is applied to the mother endoscope (not illustrated) having the above-described configuration. As shown in FIG. 1, the endoscope 20 in the present embodiment is configured to include an insertion portion 21 having an elongated shape and an operation portion 22 continuously provided at a proximal end of the insertion portion 21.

In the insertion portion 21, a distal end member 23 is provided on a distal end side, and a flexible tube portion 25 is formed on the distal end member 23 so as to be continuously provided.

In an interior of the distal end member 23, for example, an observation optical system connected with an image guide bundle and an illumination optical system configured to forward emit illumination light transmitted using a light guide bundle are provided, although illustration is omitted. An observation opening 41*a* (see FIG. 2) on which front faces of the observation optical system and the illumination optical system are exposed is formed on a front face of the distal end member 23. The observation opening 41*a* communicates with an observation hole 41 (see FIG. 5 and the like) configured to allow insertion of the insertion portion 21.

Note that the endoscope 20 in the present embodiment is a so-called front-viewing endoscope in which optical axes of an image pickup optical system and the illumination optical system are set in a long axis direction of the insertion portion 21.

Further, a channel opening 42*a* (see FIG. 2) corresponding to a suction tube 28*a* (described later; see FIG. 1) inserted into the insertion portion 21 and a treatment instrument channel (described later; see reference numeral 42 in FIG. 5), and a pair of water feeding openings 43*a* (see FIG. 2) corresponding to a water feeding tube 28*b* (described later; see FIG. 1) inserted into the insertion portion 21 are formed on the front face of the distal end member 23.

The flexible tube portion 25 is formed by a tube 35 (see FIG. 3 and the like) formed in a passively bendable manner and having flexibility. The tube 35 extends from the distal end side to the proximal end side in the long axis direction.

An active bending portion is integrally formed at a predetermined region of the distal end side of the tube 35. The active bending portion is inserted into the insertion portion 21, and can actively bend the tube 35 by an action of a bending wire 34 (described later; see FIG. 3 and the like) for bending the tube 35 when a traction operation is performed. In other words, a so-called multi-lumen tube in which the flexible tube portion 25 capable of being passively bent and the active bending portion capable of being actively bent are integrally formed is applied to the tube 35.

Note that more detailed configurations of vicinities of distal ends of the distal end member 23 and flexible tube portion 25 in the insertion portion 21 of the endoscope 20 in the present embodiment will be described later.

The operation portion 22 is configured to include a pair of bending operation knobs 26 for performing a bending operation of the bending portion that forms a part of the distal end side of the flexible tube portion 25, a treatment instrument insertion portion 27 and the like.

A tube group 28 including the image guide bundle, the light guide bundle, the suction tube 28*a* and the water feeding tube 28*b* that are inserted into the insertion portion 21 is inserted into the interior of the operation portion 22, and extends from the operation portion 22.

Note that the endoscope 20 in the present embodiment can be configured such that an image pickup unit (not illustrated) is arranged in the interior of the distal end member 23 or the interior of the operation portion 22. In the case where such a configuration is employed, an image-pickup signal cable connected with the image pickup unit extends from the operation portion 22, instead of the image guide bundle. In this case, the image-pickup signal cable is included in the above tube group.

Figure 2:
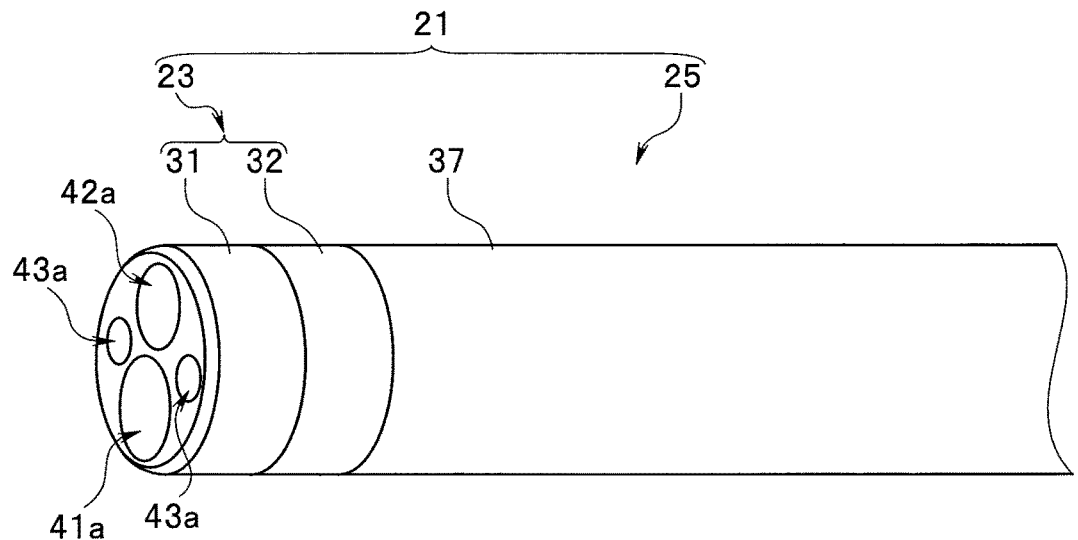
FIG. 2 is an external perspective view showing a vicinity of a distal end portion of an insertion portion of an endoscope in FIG. 1.
Figure 3:
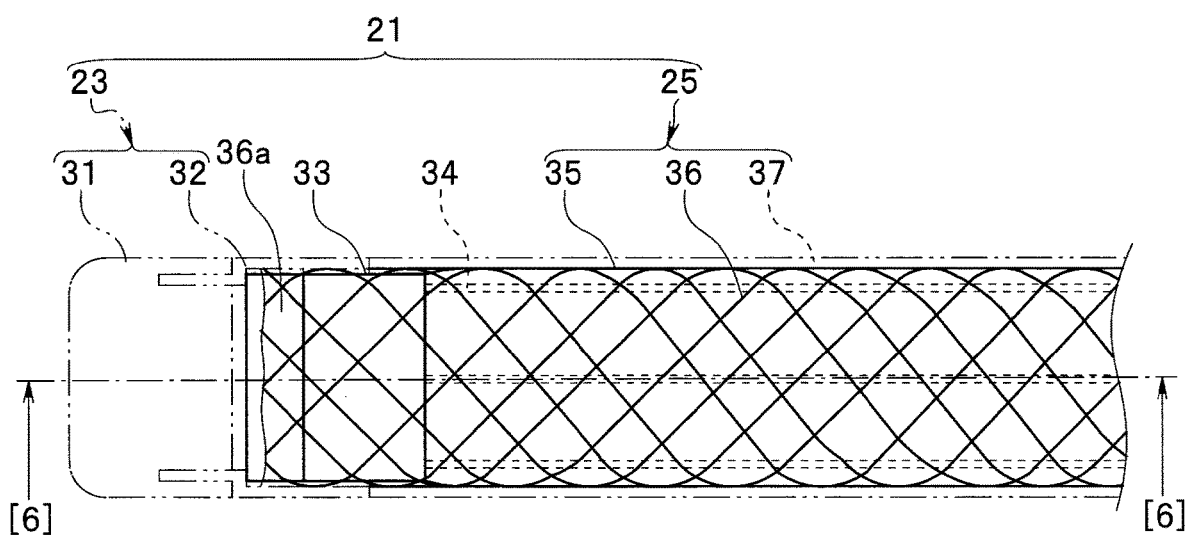
FIG. 3 is a plan view showing a state where a distal end member and an outer sleeve that configures a flexible tube portion are removed in the endoscope in FIG. 1.
Figure 4:
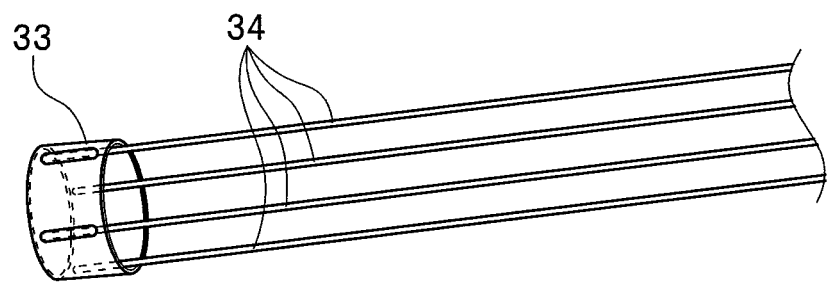
FIG. 4 is an external perspective view showing only a wire bonding ring of members that configure the distal end portion in the endoscope in FIG. 1.
Figure 5:
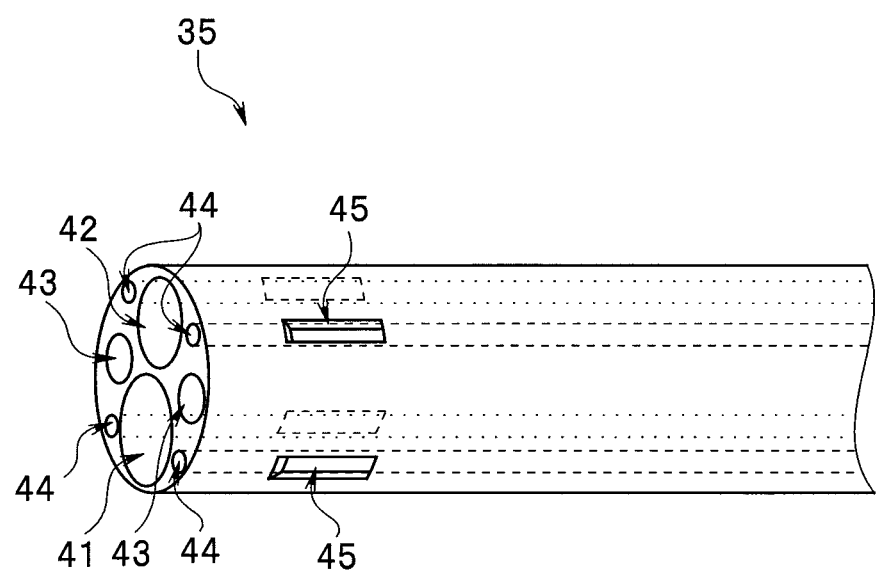
FIG. 5 is an external perspective view showing a vicinity of a distal end portion of only a multi-lumen tube of members that configure the flexible tube portion in the endoscope in FIG. 1.
Figure 6:
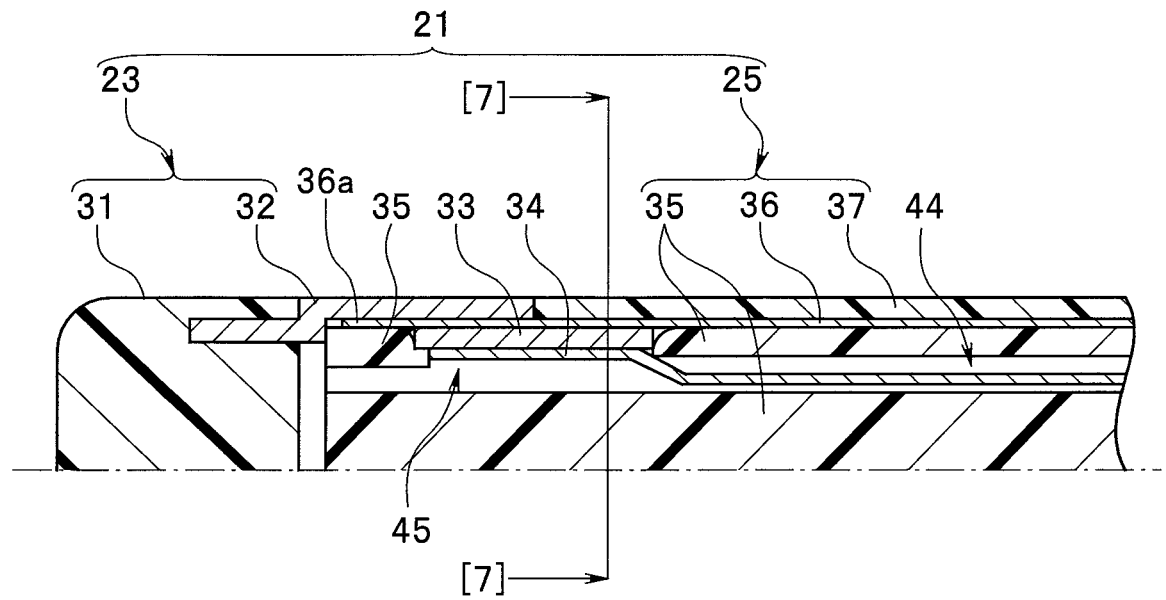
FIG. 6 is a half-sectional view of a vicinal part of the distal end portion of the insertion portion of the endoscope in FIG. 1.
Figure 7:
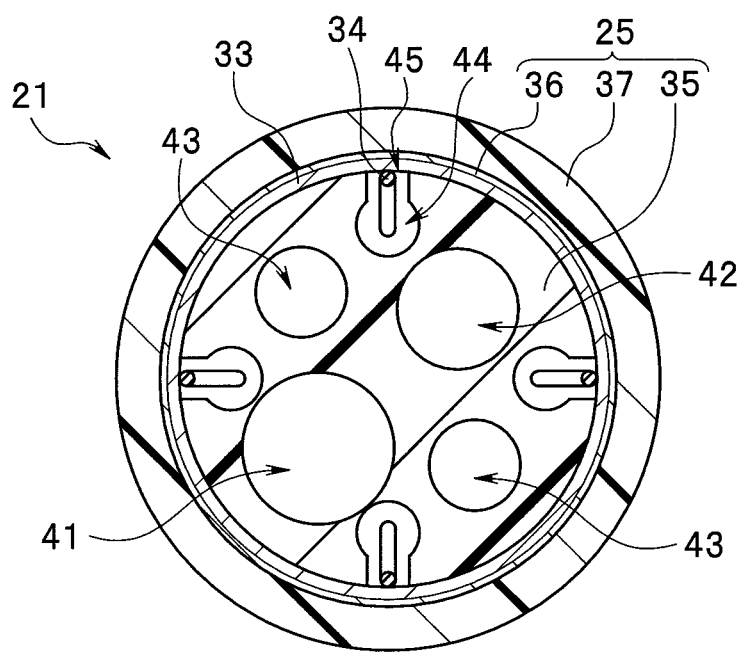
FIG. 7 is a sectional view taken along line [7]-[7] in FIG. 6.

The configuration of the vicinity of the distal end including the distal end member 23 of the insertion portion 21 of the endoscope 20 configured in this way will be described below. FIG. 2 is an external perspective view showing the vicinity of the distal end portion of the insertion portion of the endoscope in the present embodiment. FIG. 3 is a plan view showing a state where the distal end member and the outer sleeve that configures the flexible tube portion are removed in the endoscope in FIG. 1. Note that the removed members are shown by two-dot chain lines in FIG. 3. FIG. 4 is an external perspective view showing only a wire bonding ring of members that configure the distal end portion in the endoscope in FIG. 1. FIG. 5 is an external perspective view showing the vicinity of the distal end portion of only the multi-lumen tube of members that configure the flexible tube portion in the endoscope in FIG. 1. FIG. 6 is a half-sectional view of a vicinal part of the distal end portion of the insertion portion of the endoscope in FIG. 1. Note that FIG. 6 shows only an upper half portion from a long axis directional center of a section taken along line [6]-[6] (long axis directional center) in FIG. 3. FIG. 7 is a sectional view taken along line [7]-[7] in FIG. 6. Note that FIG. 7 shows a whole section of a corresponding part in the insertion portion instead of showing only a section corresponding to the half section in FIG. 6.

The vicinity of the distal end that includes the distal end member 23 of the insertion portion 21 of the endoscope 20 is configured by combining component members such as the distal end member 23, the flexible tube portion 25 and a wire bonding ring 33(not illustrated in FIG. 2; see FIG. 3 and the like).

In the distal end member 23, a distal end resin portion 31 and a distal end metal portion 32 are integrally formed by insert molding, for example. Here, the distal end resin portion 31 is composed of rigid resin, and includes the observation opening 41*a*, the channel opening 42*a*, the pair of water feeding openings 43*a* and the like. The distal end metal portion 32 is a metallic formed component formed so as to include a buried part buried in a part near an outer circumference of the distal end resin portion 31 and integrated with the distal end resin portion 31 and a metallic annular portion extending from the buried part in a direction along a central axis of the distal end resin portion 31 and formed such that an outer circumference surface of the metallic annular portion is roughly flush with an outer circumference surface of the distal end resin portion 31.

As shown in FIG. 3, the flexible tube portion 25 is configured mainly by the tube 35, a braided tube 36 and an outer sleeve 37.

As shown in FIG. 5, for example, the tube 35 is a multi-lumen tube including the observation hole 41 configured to allow insertion of a signal line and the like of the image guide bundle or the image pickup unit, the light guide bundle (not illustrated) and the like from the distal end of the insertion portion 21 to the proximal end of the insertion portion 21, a channel hole 42 configured to function as a suction channel or a treatment instrument channel, a pair of water feeding holes 43 each of which is an insertion hole for the water feeding tube 28*b*, and four wire insertion holes 44 configured to allow insertion of four wires 34 (described later; see FIG. 4, FIG. 6 and like) connected with the pair of the bending operation knobs 26 such that each of the four wires 34 can move in an axial direction. The tube 35 is formed by a deformable flexible member.

Note that the above distal end member 23 is continuously provided at the distal end of the flexible tube portion 25. At this time, the observation hole 41 of the tube 35 is disposed so as to communicate with the observation opening 41a of the distal end member 23, the channel hole 42 of the tube 35 is disposed so as to communicate with the channel opening 42a of the distal end member 23, and the pair of the water feeding holes 43 of the tube 35 is disposed so as to communicate with the pair of the water feeding openings 43a of the distal end member 23.

The wire bonding ring 33 that is a circular member is fit to an outer circumference surface at a vicinity of a distal end part of the tube 35. In other words, the tube 35 is inserted into the wire bonding ring 33. For correspondence to the insertion, an insertion hole 45 configured to cause an outer surface and each wire insertion hole 44 to communicate with each other is formed at the vicinity of the distal end part of the tube 35. Thereby, when the wire bonding ring 33 is disposed so as to be fit at the vicinity of the distal end part of the tube 35, each of the plurality of bending wires 34 extending from the wire bonding ring 33 passes through the insertion hole 45, and is inserted into the wire insertion hole 44.

The braided tube 36 is a tubular member formed in a tubular shape as a whole by weaving an element wire formed of metal, a carbon-based fiber or the like in a resin layer in a grid pattern. The braided tube 36 is provided so as to cover the outer surface of the tube 35.

The outer sleeve 37 is an elastic tube provided so as to cover an outer surface of the braided tube 36 and configuring an external facing member of the flexible tube portion 25. An outer diameter of the outer sleeve 37 is formed so as to be roughly the same as diameters of the distal end resin portion 31 of the distal end member 23 and the metallic annular part of the distal end metal portion 32. In an assembled state where the flexible tube portion 25 is joined to the distal end member 23, the wire bonding ring 33 is internally provided in the distal end metal portion 32. At this time, a gap between an inner surface of a metallic lead tube part of the distal end metal portion 32 and an outer surface of the wire bonding ring 33 is adhesively fixed in a watertight manner, using a member configured to maintain watertightness, for example, using an adhesive, with the braided tube 36 interposed. Furthermore, similarly, a gap between a distal end of the outer sleeve 37 and a proximal end surface of the distal end metal portion 32 is bonded in a watertight manner, using a member configured to maintain watertightness, for example, using an adhesive. In addition, similarly, a gap between the outer sleeve 37 and the wire bonding ring 33 is bonded in a watertight manner, using a member configured to maintain watertightness, for example, using an adhesive.

The wire bonding ring 33 is a circular member shown in FIG. 4, and is formed using a rigid material such as a metallic member including a stainless steel, for example. On an inner circumference surface of the wire bonding ring 33, respective one ends of the four bending wires 34 are bonded at roughly equally spaced positions (for example, at intervals of a rotation angle of about 90 degrees) in a circumferential direction. Each bending wire 34 extends in one direction parallel to a central axis of the wire bonding ring 33.

An outer diameter of the wire bonding ring 33 is formed so as to be roughly the same as an outer diameter of the tube 35 of the above flexible tube portion 25. As described above, the wire bonding ring 33 is arranged so as to be fit at the vicinity of the distal end portion of the tube 35. In other words, the tube 35 is inserted into the wire bonding ring 33. At this time, the four bending wires 34 extending from the wire bonding ring 33 are disposed so as to be inserted into the wire insertion holes 44 through the insertion holes 45 of the tube 35, respectively (see FIG. 6).

Note that when the wire bonding ring 33 is disposed so as to be fit at the vicinity of the distal end portion of the tube 35, the wire bonding ring 33 is disposed such that the distal end part of the tube 35 protrudes by a slight quantity toward a distal end side in the axial direction of the tube 35 and is exposed (see FIG. 3).

On the tube 35 in this state (on the tube 35 in the state where the wire bonding ring 33 is disposed so as to be fit to the distal end), the braided tube 36 is disposed so as to cover the wire bonding ring 33. At this time, as shown in FIG. 3, the braided tube 36 covers a whole surface on an outer circumference side of the wire bonding ring 33, and a distal end edge portion 36a of the braided tube 36 is disposed so as to cover a part of the distal end protrusion part of the tube 35, in other words, the tube 35 is inserted into the braided tube 36.

When the flexible tube portion 25 is joined to the distal end member 23, the braided tube 36 and the tube 35 in the above-described state are fit into an inside of the distal end metal portion 32 of the distal end member 23. At this time, as shown in FIG. 6, the distal end edge portion 36a of the braided tube 36 is disposed so as to be fixed while being sandwiched between an inner surface of the distal end metal portion 32 and an outer surface of the distal end protrusion part of the tube 35.

An outer surface of the tube 35 and braided tube 36 in this state is sheathed with the outer sleeve 37. In other words, the outer sleeve 37 is fixed on the proximal end side of the distal end member 23, so as to cover the braided tube 36 and the wire bonding ring 33. While tightly contacting with the proximal end surface of the distal end metal portion 32, the distal end edge portion of the outer sleeve 37 is bonded in a watertight manner, using a member configured to maintain watertightness, for example, using an adhesive.

Figure 8:
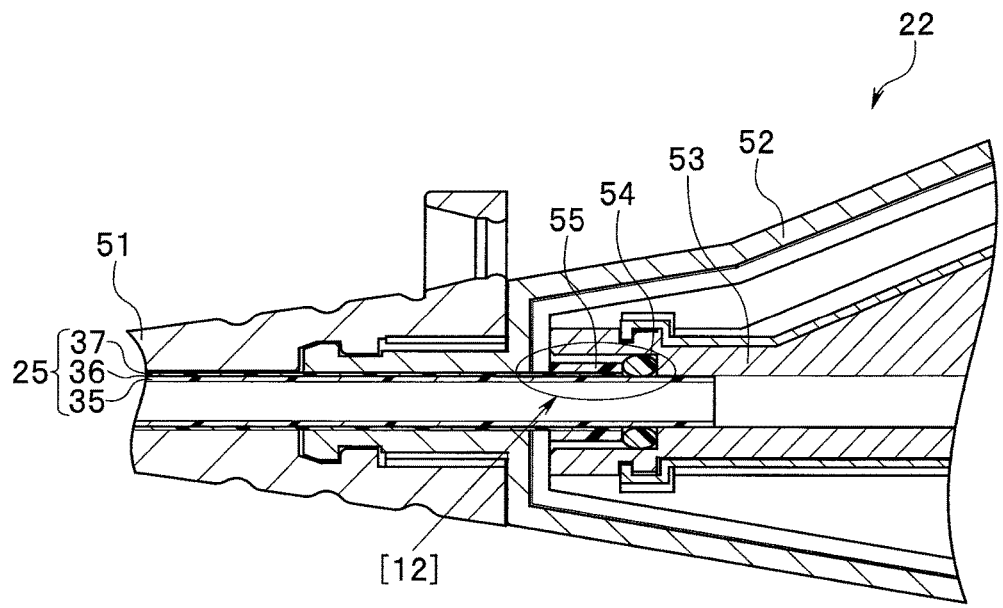
FIG. 8 is a sectional view showing a configuration of a vicinity of a proximal end of the flexible tube portion of the endoscope in FIG. 1.
Figure 9:
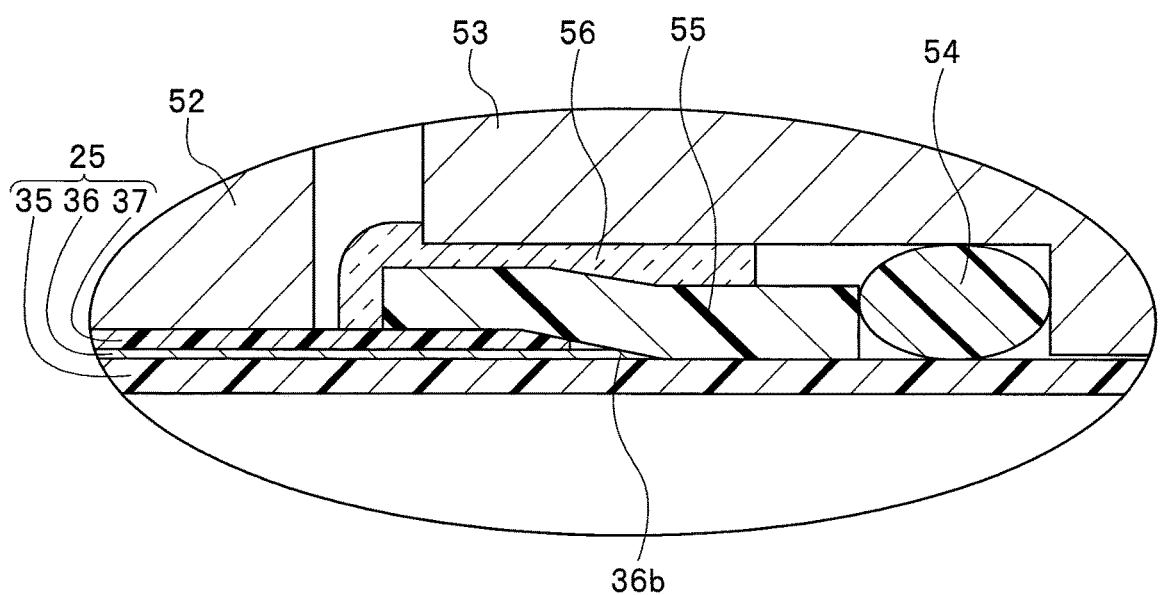
FIG. 9 is a principal-portion enlarged sectional view showing a part shown by reference numeral [12] in FIG. 8, as an enlarged view.

A configuration of a vicinity of a proximal end of the flexible tube portion 25 will be described below. FIG. 8 is a sectional view showing the configuration of the vicinity of the proximal end of the flexible tube portion of the endoscope in the present embodiment. FIG. 9 is a principal-portion enlarged sectional view showing a part shown by reference numeral [12] in FIG. 8, as an enlarged view.

A proximal end part of the flexible tube portion 25 is inserted into a bend preventing portion 51, and thereafter is inserted into an interior of an operation portion external face 52 of the operation portion 22. At the proximal end part of the flexible tube portion 25, as shown in FIG. 9, a proximal end portion of the outer sleeve 37 and a proximal end edge portion 36b of the braided tube 36 are provided so as to be fixed to an internal fixation member 53 of the operation portion 22, and is inserted into a silicone tube 55 provided for positioning fixation of an O-shaped ring 54. Note that the tube 35 passes through the silicone tube 55 and extends from the silicone tube 55 at this time. By this configuration, the proximal end edge portion 36b of the braided tube 36 is stably fixed while being sandwiched between an inner surface of the silicone tube 55 and an outer surface of the tube 35.

In this state, as shown in FIG. 9, an adhesive 56 is applied to outer surfaces of the internal fixation member 53, the silicone tube 55 and the outer sleeve 37, and by curing of the adhesive 56, the above respective component members (53, 55, 37) are fixed to each other. Accordingly, by such a configuration, at the proximal end edge portion 36b of the braided tube 36, a stable shape in a state where fraying of the woven portion is prevented is maintained.

As described above, according to the above first embodiment, in the endoscope 20 that is the insertion apparatus including the insertion portion 21 including the flexible tube portion 25 using the multi-lumen tube (35), the distal end edge portion 36a of the braided tube 36 in the flexible tube portion 25 is disposed on the inner circumference side of the distal end metal portion 32 that is the rigid member of the distal end member 23, and the distal end edge portion 36a is stably fixed while being sandwiched between the inner surface of the distal end metal portion 32 that is the rigid member and the distal end outer surface of the tube 35. At this time, the outer circumference side of the wire bonding ring 33 is sheathed with the braided tube 36.

By this configuration, in the endoscope 20 in the present embodiment, the distal end edge portion 36a of the braided tube 36 is fixed in a stable sate, on the inside of the distal end metal portion 32 that is the rigid member, and therefore, it is possible to surely prevent a state where the distal end edge portion 36a of the braided tube 36 protrudes from the outer surface of the outer sleeve 37 or the like and is exposed, for example, by cutting through the member on the outer surface side. Further, thereby, it is possible to secure the watertight property of the distal end portion while restraining the increase in the diameter of the insertion portion 21, and at the same time, it is possible to secure a safe and suitable insertion properly.

Further, it is possible to avoid the distal end edge portion 36a of the braided tube 36 from breaking the outer sleeve 37, and since the distal end edge portion 36a of the braided tube 36 is not disposed at the part on an inside of the outer sleeve 37, it is possible to contribute to the decrease in the thickness of the outer sleeve 37 at that part. Accordingly, it is possible to reduce the diameter of the insertion portion 21 as a whole, and consequently, it is possible to secure the enhancement of the insertion property of the endoscope 20 as the insertion apparatus for the subject.

Furthermore, it is not necessary to perform, particularly, thread binding fixation, brazing processing, soldering treatment or the like, as stable fixation means for the distal end edge portion 36a of the braided tube 36, and therefore, it is possible to prevent a partial increase in diameter, and consequently, it is possible to contribute to the reduction in diameter of the insertion portion 21.

Furthermore, since the above various fixation processing treatments and the like are unnecessary, it is possible to simplify assembly steps for the whole of the endoscope 20, and to reduce production equipment and production steps.

Second Embodiment

Next, a second embodiment of the present invention will be described below. Basically, a configuration of the present embodiment is roughly the same as the configuration of the above-described first embodiment. In the present embodiment, the configuration of the vicinity of the distal end portion of the insertion portion is different only in that the braided tube 36 is configured to be disposed on an inside of the wire bonding ring 33. The other configuration is roughly the same as the configuration of the above-described first embodiment.

Accordingly, in the following description, only the point different from the above-described first embodiment will be described in detail, parts having the same configurations as the configurations of the above-described first embodiment are denoted by the same reference numerals, and detailed descriptions of the parts will be omitted.

Figure 10:
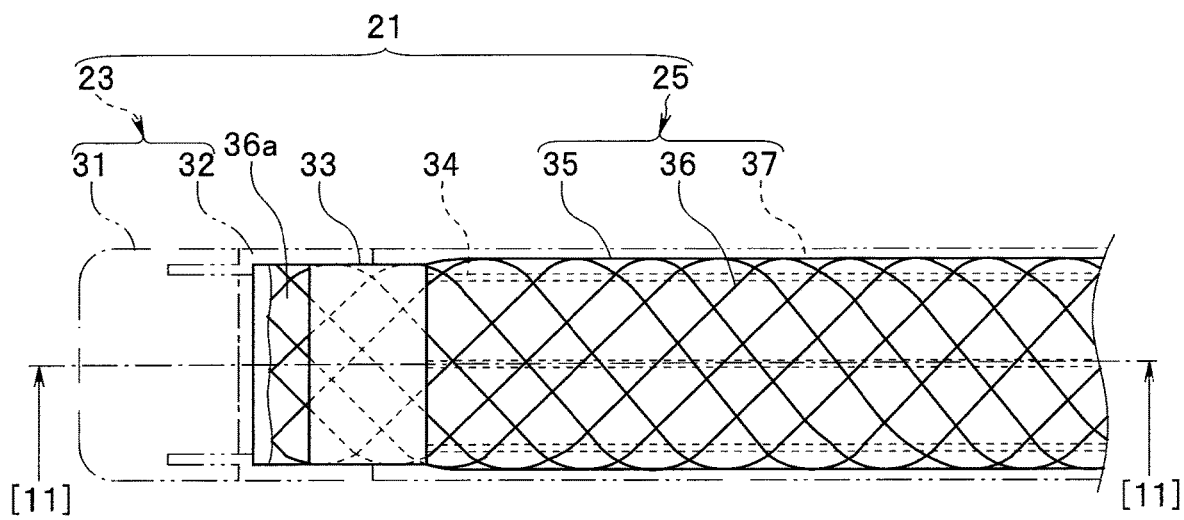
FIG. 10 is a plan view showing a state where a distal end member and an outer sleeve that configures a flexible tube portion are removed in an endoscope in a second embodiment of the present invention.
Figure 11:
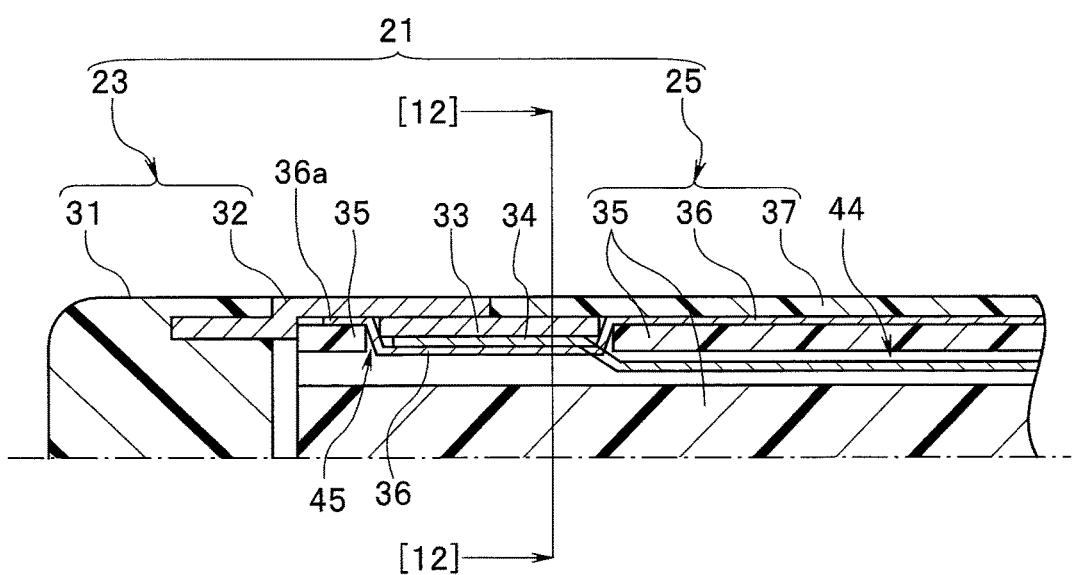
FIG. 11 is a half-sectional view of a vicinal part of a distal end portion of an insertion portion of the endoscope in FIG. 10.
Figure 12:
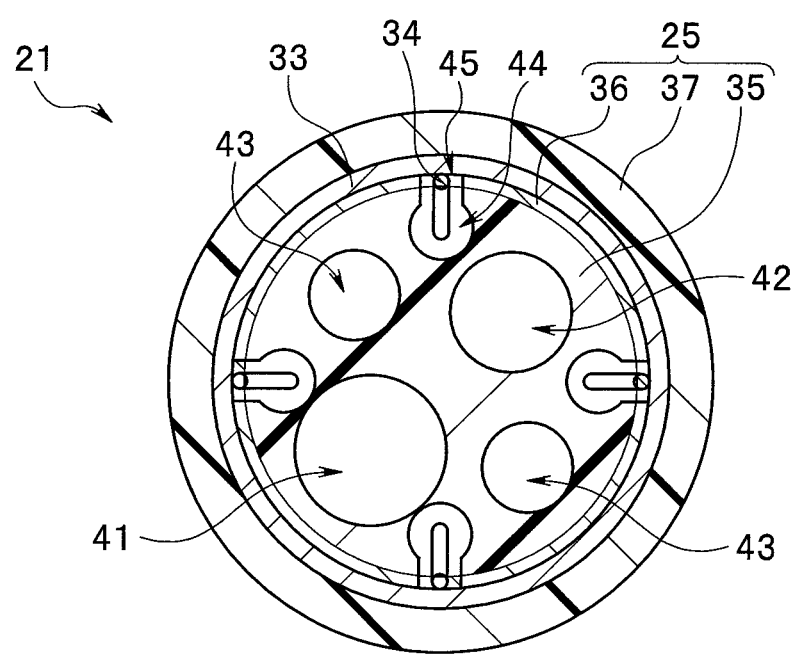
FIG. 12 is a sectional view taken along line [12]-[12] in FIG. 11.

FIG. 10 is a plan view showing a state where a distal end member and an outer sleeve that configures a flexible tube portion are removed in an endoscope in the second embodiment of the present invention. Note that the removed members are shown by two-dot chain lines in FIG. 10. FIG. 11 is a half-sectional view of a vicinal part of a distal end portion of an insertion portion of the endoscope in FIG. 10. Note that FIG. 11 shows only an upper half portion from a long axis directional center of a section taken along line [11]-[11] long axis directional center) in FIG. 10. FIG. 12 is a sectional view taken along line [12]-[12] in FIG. 11. Note that FIG. 12 shows a whole section of a corresponding part in the insertion portion instead of showing only a section corresponding to the half section in FIG. 11.

A vicinity of the distal end that includes the distal end member 23 of the insertion portion 21 of the endoscope 20 in the present embodiment is configured by combining component members such as the distal end member 23, the flexible tube portion 25 and the wire bonding ring 33, similarly to the above-described first embodiment.

In the above-described first embodiment, the wire bonding ring 33 is configured to be externally inserted to the tube 35, such that the outer surface of the wire bonding ring 33 is disposed so as to be covered with the braided tube 36, that is, such that the wire bonding ring 33 is disposed on the inside of the braided tube 36.

On the other hand, the present embodiment is different in that the wire bonding ring 33 is configured to be externally inserted to the tube 35, such that the wire bonding ring 33 is disposed so as to cover a part of the outer surface of the braided tube 36, that is, such that the wire bonding ring 33 is disposed on the outside of the braided tube 36, in other words, such that a part of the braided tube 36 is internally provided in the wire bonding ring 33. Note that in this case, the distal end edge portion 36a of the braided tube 36 is disposed at a position on the distal end side of the wire bonding ring 33. In a joined state where the distal end member 23 is attached to the distal end of the flexible tube portion 25, the distal end edge portion 36a of the braided tube 36 is disposed on the inner circumference side of the distal end metal portion 32.

By this configuration, the distal end edge portion 36a of the braided tube 36 is stably fixed at a part on the inside of the distal end metal portion 32, and therefore the distal end edge portion 36a does not protrude toward the outer surface.

In the configuration of the present embodiment, the wire bonding ring 33 is disposed on the outside of the braided tube 36, in this case, each of the four bending wires 34 passes through the gap of the braided tube 36, and is disposed on the inside of the braided tube 36. Therefore, the gaps of the mesh of the braided tube 36 are relatively sparsely formed, and for example, the braided tube 36 is formed so as to have gaps through which the bending wires 34 can pass. Furthermore, the bending wires 34 pass through the insertion holes 45 of the tube 35, and are inserted into the wire insertion holes 44. By this configuration, each of the four bending wires 34 is configured to be capable of surely performing a prescribed action with no difficulty.

As described above, according to the above second embodiment, it is possible to obtain the same effect as the effect of the above-described first embodiment. Furthermore, according to the present embodiment, since the wire bonding ring 33 is configured to be disposed on the outside of the braided tube 36, it is possible to contribute to a further decrease in the outer diameter of the insertion portion 21.

The present invention is not limited to the above-described embodiments, and naturally, various modifications and applications can be performed without departing from the spirit of the invention. Furthermore, in the above embodiments, inventions in various stages are included, and various inventions can be extracted by appropriate combinations of a plurality of disclosed component requirements. For example, even when some component requirements are excluded from all component requirements shown in the above embodiments, the configuration in which the component requirements are excluded can be extracted as an invention as long as the problem to be solved by the invention can be solved and the effects of the invention can be obtained. Furthermore, component elements in different embodiments may be appropriately combined. The invention is limited only by the attached claims, and is not restricted by particular embodiments.

What is claimed is:

1. An insertion apparatus comprising:
    a bendable tube;
    a distal end body covering a distal end of the bendable tube;
    a braided tube, the bendable tube is inserted into the braided tube, a distal end of the braided tube being disposed between the distal end body and the bendable tube; and
    a wire configured to bend the bendable tube, wherein
    the wire penetrates radially into an interior of the braided tube.

2. The insertion apparatus according to claim 1, further comprising a ring disposed inside the distal end body, the bendable tube being inserted into the ring.

3. The insertion apparatus according to claim 2, further comprising an elastic tube fixed on a proximal end side of the distal end body, the elastic tube covering the braided tube and the ring.

4. The insertion apparatus according to claim 2, wherein the wire is fixed to the ring.

5. The insertion apparatus according to claim 2, wherein the braided tube covers the ring.

6. The insertion apparatus according to claim 2, wherein a part of the braided tube is internally provided in the ring.

7. The insertion apparatus according to claim 2, further comprising an adhesive configured to maintain watertightness arranged in a gap between the distal end body and the ring.

8. The insertion apparatus according to claim 3, further comprising an adhesive configured to maintain watertightness arranged between the elastic tube and the ring, the adhesive is arranged between the distal end body and the elastic tube.

9. The insertion apparatus according to claim 1, wherein the insertion apparatus is a disposable endoscope configured to be discarded after use.

10. An endoscope comprising:
    a bendable tube;
    a distal end body covering a distal end of the bendable tube;
    a braided tube, the bendable tube is inserted into the braided tube, a distal end of the braided tube being disposed between the distal end body and the bendable tube; and
    a wire configured to bend the bendable tube, wherein
    the wire penetrates radially into an interior of the braided tube.

11. The endoscope according to claim 10, further comprising a ring disposed inside the distal end body, the bendable tube being inserted into the ring.

12. The endoscope according to claim 11, wherein the braided tube covers the ring.

13. The endoscope according to claim 11, wherein a part of the braided tube is internally provided in the ring.

14. The endoscope according to claim 11, further comprising an adhesive configured to maintain watertightness arranged between the distal end body and the ring.

15. The endoscope according to claim 12, further comprising an adhesive configured to maintain watertightness arranged between the elastic tube and the ring, the adhesive is arranged between the distal end body and the elastic tube.

16. The endoscope according to claim 10, wherein the endoscope is a disposable endoscope configured to be discarded after use.

17. The insertion apparatus according to claim 1, wherein a hole is disposed in the tube, the wire is configured to extend within the hole.

18. The endoscope according to claim 10, wherein a hole is disposed in the tube, the wire is configured to extend within the hole.

19. The insertion apparatus according to claim 1, wherein the bendable tube is a multi-lumen tube.

20. The endoscope according to claim 10, wherein the bendable tube is a multi-lumen tube.

* * * * *